United States Patent
Brand et al.

(12) 
(10) Patent No.: US 6,218,577 B1
(45) Date of Patent: Apr. 17, 2001

(54) ENEGETIC HYDRAZINIUM SALTS

(75) Inventors: Adam J. Brand, Palmdale; Gregory W. Drake, Lancaster, both of CA (US)

(73) Assignee: The United States of America as represented by the Secretary of the Air Force, Washington, DC (US)

(*) Notice: Subject to any disclaimer, the term of this patent is extended or adjusted under 35 U.S.C. 154(b) by 0 days.

(21) Appl. No.: 09/356,227

(22) Filed: Jul. 16, 1999

Related U.S. Application Data

(60) Provisional application No. 60/093,733, filed on Jul. 20, 1998.

(51) Int. Cl.$^7$ .................................................. C07C 241/02
(52) U.S. Cl. .............................................................. 564/464
(58) Field of Search ................................ 564/464; 149/36, 149/122

(56) References Cited

U.S. PATENT DOCUMENTS

| | | | | |
|---|---|---|---|---|
| 3,297,747 | * | 1/1967 | Thornton et al. | 564/310 |
| 3,314,837 | * | 4/1967 | Heubusch | 525/410 |
| 4,310,696 | * | 1/1982 | Hojo et al. | 564/464 |

* cited by examiner

*Primary Examiner*—Johann Richter
*Assistant Examiner*—Brian J. Davis
(74) *Attorney, Agent, or Firm*—Thomas C. Stover

(57) ABSTRACT

Provided is a salt of hydroxyethylhydrazine (HEH) of $[HO-CH_2-CH_2-NH_2-NH_2^+][X^-]$ or $[HO-CH_2-CH_2-NH_2-NH_3^{2+}][X^-]_2$, where $X=NO_3$, $ClO_4$, $N(NO_2)_2$ or $C(NO_2)_3$ and method of making same.

19 Claims, No Drawings

ENEGETIC HYDRAZINIUM SALTS

This application claims priority from U.S. provisional application Ser. No. 60/093,733 filed Jul. 20, 1998.

STATEMENT OF GOVERNMENT INTEREST

The invention described herein can be manufactured and used by or for the Government for governmental purposes without the payment of any royalty thereon.

BACKGROUND OF THE INVENTION

1. Field of the Invention

This invention relates to hydrazine related salts particularly those of high energy.

2. Description of Related Art

Hydrazine is considered the state-of-the-art monopropellant for on-orbit satellite propulsion systems. However, a major drawback in the use of hydrazine resides in its inherent high vapor pressure at ambient temperatures resulting in high vapor toxicity. This toxicity results in a considerable investment in equipment and handling (safety requirements) to fuel and unload propulsion systems which incorporate hydrazine. Consequently, new ingredients are sought which can yield equivalent or superior specific impulse performance to that of hydrazine, yet have more desirable physical properties and significantly reduced toxicity.

Also heavy metal compounds have been targeted by both industry and government for reduction, and if possible, elimination of use. Certain explosives and initiators still contain heavy metals which can cause environmental and health concerns in their use and in their final disposal due to their inherent toxicity. Thus, there are environmental benefits to the use of these new salts as explosives or explosive ingredients.

In the prior art is U.S. Pat. No. 5,485,722 to Schmidt et al (1996), which discloses the decomposition of hydroxylammonium nitrate (HAN) monopropellant via metal catalyst. The disclosure pertains to monopropellant comprised of HAN as the primary component and suggests a list of possible organic or inorganic amine fuels as minor components. Included in the list of minor components is hydroxyethylhydrazinium nitrate (HEHN) but no results are noted with HEHN. While a HAN-based monopropellant can represent an approach to improved performance over hydrazine, experimental evidence shows such propellant is susceptible to a significant degree of thermal instability.

Also in the prior art is U.S. Pat. No. 5,433,802 to Rothgery et al (1995), which discloses the use of reduced volatility substituted hydrazine compounds in liquid propellants. The disclosure pertains to a liquid or gel bi-propellant comprised of an oxidizer, various nitrogen oxides or fuming nitric acid, and a fuel of a substituted hydrazine, with 2-hydroxyethylhydrazine being mentioned as a possible fuel. While this system can represent an approach to improved performance over hydrazine, it is a bi-propellant system, with fuel and oxidizer being held separately until their immediate use.

Accordingly there is need and market for a hydrazine replacement of reduced vapor toxicity that overcomes the above prior art shortcomings.

There has now been discovered a new energetic hydrazinium salts of such reduced toxicity, with enhanced stability and performance and method of making same.

SUMMARY OF THE INVENTION

Broadly, the present invention provides a method for preparing at least one hydroxyethylhydrazine (HEH) salt comprising, reacting the following:

$HO-CH_2-CH_2-NH-NH_2 + m\ HX \rightarrow [HO-CH_2-CH_2-NH_2-NH_2^+][X^-]$ or $[HO-CH_2-CH_2-NH_2-NH_3^{2+}][X^-]_2$ where $HX=HNO_3$, $HClO_4$, $HN(NO_2)_2$ and $HC(NO_2)_3$ and $m=1$ or 2.

The invention also includes the HEH salts so made.

Definitions:

By "30–100 wt %" acid concentration is meant acid in an aqueous solution up until 100 wt % when it becomes an anhydrous solution.

All %(s) herein are wt %(s) unless otherwise indicated

DETAILED DISCRIPTION OF THE INVENTION

The new salts were made by several different routes as discussed below. The general route is through an acid-base reaction in a polar solvent system between the relatively strong base, 2-hydroxyethylhydrazine and a strong acid of a desired energetic anion. The general reactions are as follows:

For 1:1 salts:

$HO-CH_2-CH_2-NH-NH_2 + HX \rightarrow [HO-CH_2-CH_2-NH_2-NH_2^+][X^-]$ where $HX=HNO_3$, $HClO_4$, $HN(NO_2)_2$ or $HC(NO_2)_3$ For 1:2 salts:

$HO-CH_2-CH_2-NH-NH_2 + 2\ HX \rightarrow [HO-CH_2-CH_2-NH_2-NH_3^{2+}][X^-]_2$ where $HX=HNO_3$ or $HClO_4$ The above inventive reactions are suitably carried out in an inert, dry atmosphere, (nitrogen and argon are suitable materials) from $-25°$ C. to $+25°$ C. and in a polar solvent system which includes, methanol, ethanol, isopropanol, n-propanol, n-butanol, water or acetonitrile.

The following examples are intended to illustrate the invention and should not be construed in limitation thereof.

EXAMPLE 1

Formation of 2-hydroxyethylhydrazinium nitrate $[HO-CH_2-CH_2-NH_2-NH_2]^+[NO_3]^-$:

To a preweighed Schlenk flask equipped with a #15 O-ring joint and matching glass cap, a 4 mm teflon screw cap type valve, and a teflon stirbar, 0.3160 grams; 4.152 mmoles of 2-hydroxyethylhydrazine (99% Aldrich) were added via a pipet inside a nitrogen filled drybox. Outside the drybox, the sealed-off flask was attached to a double manifold line equipped with high vacuum and dry nitrogen gas. The flask was vacuum evacuated for a short time and then purged with nitrogen gas. Methanol, 10 ml (Aldrich, 99%, Reagent grade, dried over Na metal and distilled under nitrogen), was added to the flask under nitrogen flow via a plastic syringe equipped with a teflon needle, resulting in a clear, homogenous solution of the 2-hydroxyethylhydrazine. With vigorous stirring, nitric acid ($HNO_3$, Aldrich reagent grade, 70.0% by weight) 0.3824 grams (4.248 mmoles) was added via pipet under nitrogen flow to the 2-hydroxyethylhydrazine/methanol solution. An exothermic reaction was noted, and the solution was stirred for 1 hour at ambient temperature. After this time, the stirbar was removed, and the solvent removed by vacuum for 18 hours at ambient temperature. A clear, viscous oil remained which was evacuated to constant weight in a vacuum dessicator in the presence Of $P_4O_{10}$. Yield, 0.5623 g; theoretical 0.5776 grams, 97.4%.

The above example is amplified as follows:

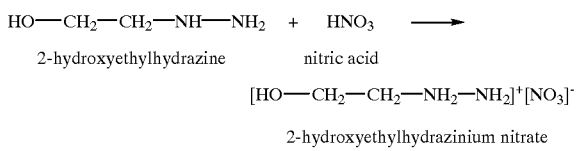

EXAMPLE 2
Formation of 2-hydroxyethylhydrazinium perchlorate [HO—CH$_2$—CH$_2$—NH$_2$—NH$_2$]$^+$[ClO$_4$]$^-$:

To a preweighed Schlenk flask equipped with a #15 O-ring joint and matching glass cap, a 4mm teflon screw cap type valve and a teflon stirbar, was charged with 0.8363 grams (10.98 mmoles) inside a nitrogen filled drybox, Outside the drybox, the reaction flask was attached to a double manifold as described above. Acetonitrile (Aldrich, 99.9% purity, distilled from CaH$_2$ under N$_2$, stored over 3 angstrom activated molecular sieves), 10 ml was added by a disposable syringe equipped with teflon needle under nitrogen flow. A clear homogenous solution resulted. The perchloric acid (baker Reagent grade, 70.0% by weight) 1.6400 grams (11.4 mmoles) was added by a glass pipet while the flask was under nitrogen flow. There was heat evolution upon addition. A clear homogenous solution resulted which was stirred at ambient temperature for 90 minutes. At the end of this time the stirbar was removed and the solvent removed by dynamic evacuation for 18 hours, resulted in a colorless, viscous oil. The flask and the viscous product were transferred to a vacuum dessicator containing phosphorus pentoxide, and then the contents were evacuated for an additional 24 hours, resulting in a viscous, clear oil. Yield: 1.9930 grams, theoretical 1.9765, (100.4%).

EXAMPLE 3
Formation of 2-hydroxyethylhydrazinium monodinitramide [HO—CH$_2$—CH$_2$—N$_2$H$_4$$^+$][N(NO$_2$)$_2$$^-$]:

The above synthetic approach works well for nitric and perchloric acids, however, in the case of the dinitramide salt, an alteration to the above approach must be taken. Using a strong acid cation exchange resin, one can form the acid form of dinitramide, HN(NO$_2$)$_2$ in dilute form which is eluted through the column with methanol, then reacts with 2-hydroxyethylhydrazine in the same fashion as Equation 1. Many salts of dinitramide can be used including, potassium dinitramide, ammonium dinitramide, and sodium dinitramide. This technique has been used by previously by others in the field to form other dinitramide salts. Also per the invention, trinitromethane, H—C(NO$_2$)$_3$, which is very difficult and hazardous to manipulate in its pure form, is easily handled in a dilute 1,2-dichloroethane solution. This solution is titrated with a standardized base to get an accurate measure of its concentration.

The above process is exemplified as:

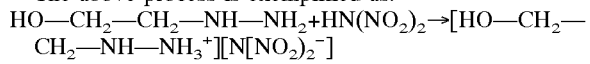

EXAMPLE 4
Formation of 2-hydroxyethylhydrazinium nitroformate [HO—CH$_2$—CH$_2$—NH$_2$—NH$_2$]$^+$[C(NO$_2$)$_3$]$^-$:

A Schlenk flask was evacuted, then charged with nitrogen gas to ambient pressure, then sealed off and its mass measured. Approximately 4 ml of trinitromethane in 1,2-dichloroethane solution (6.1070 grams of solution; .2021 grams of H—C(NO$_2$)$_3$; 1.338 mmoles), (dried over magnesium sulfate, then titrated with standardized base, 3.309% by weight) were syringed into the nitrogen filled flask. Inside a nitrogen filled drybox, a separate, preweighed Schlenk flask was charged with 0.1013 grams (1.331 mmoles) of 2-hydroxyethylhydrazine. Outside the drybox, 5 ml of dry acetonitrile was added to the 2-hydroxyethylhydrazine, dissolving it and forming a colorless, homogenous solution. A teflon stirbar was added, and then this flask and its contents were chilled in a dewar condenser containing a –22° C. slush bath (CCl$_4$/liquid N$_2$). Once this solution had reached thermal equilibrium, the nitroform solution was slowly syringed into it, with immediate formation of a bright yellow, colored reaction solution. The flask containing the nitroform solution was washed with 2×3 ml of fresh acetonitrile, and these washings were added into the reaction vessel. The flask was stirred for 1 hour at –22° C. and then slow removal of the solvent at this temperature was carried out for 9 hours. After this time the flask was transferred to a 0° C. bath and evacuated for 4 hours at this temperature, and finally the flask was allowed to warm to ambient temperature and was evacuated for 2 additional hours. A bright yellow, viscous oil was left. Yield: 0.3105 grams, theoretical 0.3034 g (102%).

EXAMPLE 5
Formation of 2-hydroxyethylhydrazinium dinitrate [HO—CH$_2$—CH$_2$—NH$_2$—NH$_3$]$^{2+}$[NO$_3$$^-$]$_2$:

Reaction was carried out essentially the same manner as the mononitrate salt, except that the reaction was carried out at 0° C. to control exothermic nature of the reaction. That is, 2-hydroxyethylhydrazine, 0.5399 g (7.09 mmoles) was charged into a preweighed Schlenk flask inside a nitrogen-filled drybox. Outside the drybox, the flask was attached to a double manifold line, evacuated then flushed with N$_2$, 10 ml of dry acetonitrile added and a teflon stirbar added. A solution of nitric acid (Aldrich, A C. S. reagent grade, 70% by weight) 1.3500 grams (15.0 mmoles) was added via pipet under nitrogen flow. After stirring one hour at 0° C., there were two distinct layers in solution. The stirbar was removed, and evacution at 0° C. was carried out for 8 hours, followed by 5 hours evacuation at ambient temperature, resulting in a white crystalline mass. Yield: 1.4552 grams; theoretical 1.4339 grams (101%).

EXAMPLE 6
Formation of 2-hydroxyethylhydrazinium diperchlorate [HO—CH$_2$—CH$_2$—NH$_2$—NH$_3$]$^{2+}$[ClO$_4$$^-$]$_2$:

2-hydroxyethylhydrazine, 0.3884 grams (5.10 mmoles) was added to a preweighed Schlenk flask inside a nitrogen-filled drybox. Outside the drybox, the flask was attached to a double manifold line, evacuated, then charged with nitrogen gas. Dry acetonitrile (10 mL) was added to the 2-hydroxyethylhydrazine along with a teflon stirbar, which resulted in a colorless, homogenous solution. Perchloric acid (Baker Reagent grade, 70.0% by weight) 1.4620 grams was added via a pipet under nitrogen flow, resulting in a colorless reaction solution. After 30 minutes of stirring at ambient temperature, two, clear solution layers had formed in the flask. The stirbar was removed and reaction flask evacuated at 0° C. for 12 hours, followed by one hour evacuation at ambient temperature, whereupon a viscous oil was recovered. Flask and viscous contents were transferred to a vacuum dessicator containing a copious amount of phosphorus pentoxide which was then evacuated for 18 hours at ambient temperature leaving a crop of white, extremely friction and impact sensitive crystals. Yield: 1.4165 grams; theoretical 1.4139 grams (100%.)

Thus it can be seen that the energetic salts (of 2-hydroxyethyl hydrazine) of the invention, demonstrate many favorable physical and chemical properties for potential use in a variety of applications. The 1:1 salts of 2-hydroxyethylhydrazine have negligible vapor pressure (insignificant vapor toxicity), high density, and low melting points (<25° C.) which lend themselves well as energetic candidate ingredients in monopropellants. When formulated with other ingredients described below, the resulting monopropellants exhibit better performance (higher energy-density), a lower melt point (<1° C.), and negligible vapor toxicity over the state-of the-art monopropellant; hydrazine. The new 1:2 salts (doubly protonated 2-hydroxyethyl hydrazine) are even higher in energy (balanced or near balanced combustion wise to CO, $CO_2$, $H_2O$ and $N_2$) and density and show comparable performances to well known explosive materials currently used in the field without having heavy metals present. Certain 2-hydroxyethylhydrazine salts are intrinsically clean burning (no particulates or corrosive acids) which makes gas generators another possible application for these materials. These new salts can be used alone or in mixtures with other high energy compounds and/or eutectics and/or liquid propellant formulations and/or solid propellant formulations. Such other high energy compounds would include ammonium nitrate, ammonium perchlorate, ammonium dinitramide, hydroxylammonium nitrate, hydroxylammonium dinitramide, hydroxylammonium perchlorate, lithium nitrate, lithium dinitramide, lithium perchlorate, nitric acid (30–100 wt %), inhibited red fuming nitric acid (IRFNA), and perchloric acid (30–70 wt %).

Still other (such) high energy compounds include, lithium azide, ammonium azide, hydrazinium azide, hydrazinium nitrate, hydrazinium perchlorate, hydrazinium dinitramide, guanidinium nitrate, guanidinium perchlorate and guanidinium dinitramide, to form new monopropellant(s), monopropellant ingredients, and/or new non-metal based explosives and initiators.

These inventive salts of 2-hydroxyethylhydrazine are highly energetic and have very low vapor pressure, significantly higher density, wider liquid range (for 1:1 salts), higher energy output, and significantly reduced toxicity over the state of the art, hydrazine. These new salts can also be used for new non-heavy metal explosives and initiators, devices, and as mixtures/eutectics with other known explosive materials. The energetic 2-hydroxyethylhydrazinium salts can be used as an ingredient of monopropellant compositions for on-orbit altitude and reaction control applications. Almost all of these salts possess virtually no vapor pressure nor vapor toxicity at operational temperatures. Another possible application area includes gas generator systems for emergency power units or vehicle passenger restraint systems. Certain 2-hydroxyethylhydrazinium salts are intrinsically clean burning (i.e. no particulate matter) which is a beneficial property of gas generator propellants.

Salts of the invention can also be synthesized by other methods within the scope of the present invention. Thus the use of strong acid ion exchange resins with the appropriate salt, as mentioned for the dinitramide synthesis, can also work in the syntheses of all of the materials mentioned here. Examples for starting material salts for use in ion exchange processes include, alkali metal nitrates, nitroformates and perchlorates, alkaline earth metal nitrates, nitroformates and perchlorates, ammonium and substituted ammonium nitrates, nitroformates and perchlorates, transition metal nitrates, perchlorates and nitroformates, and lanthanide nitrates, perchlorates and nitroformate salts. Metathesis type reaction with 2-hydroxyethylhydrazinium salts including, halides, sulfates, bisulfates, phosphates, carbonates, haloborates, and haloaluminates in polar solvents such as water, methanol, ethanol, acetonitrile, n-propanol, isopropanol and n-butanol with the appropriate reagent to cause precipitation of one of the two products from the reaction solution. One example can include the reaction of 2-hydroxyethylhydrazinium sulfate with barium nitrate, perchlorate or dinitramide, causing the precipitation and facile separation of barium sulfate to give the easily purified energetic 2-hydroxyethylhydrazinium salt. Another example can be the reaction of a 2-hydroxyethylhydrazinium halide ($Cl^-$, $Br^-$, $I^-$) with either silver nitrate, silver perchlorate or silver dinitramide, resulting in the precipitation of the silver halide salt from the reaction solution, whereby the precipitated silver halide salt can be easily removed from the reaction solution, giving the readily purified energetic 2-hydroxyethylhydrazinium salt. A third example can be to use the poor solubility of certain alkali metal halide salts in polar organic solvents to precipitate away reaction product salts such NaCl, NaBr, KCl, and KBr from the reaction solution to get a readily purified energetic 2-hydroxyethylhydrazinium salt.

Thus 2-hydroxyethylhydrazine (2-HEH) reacts with the above strong acids [$HNO_3$, $HClO_4$, $HN(NO_2)_2$ or $HC(NO_2)_3$] in 1:1 & 1:2 stoichiometries in various polar solvents to form the monoprotonated and the diprotonated 2-HEH salts of the conjugate bases of such acids. The above 1:1 salts are liquids at ambient temperature (about 25° C.) while the 1:2 salts are solids and all are highly energetic materials suitable for the uses noted herein.

Accordingly, such salts can be used singly or in combination with other high energy materials, listed above, for such products as non-heavy-metal explosives or initiators in mixtures, eutectics or other fomulations. Other uses include those as a monopropellant ingredient for propulsion devices, gas generators and for air bag applications.

What is claimed is:

1. A method for preparing at least one hydroxyethylhydrazine (HEM) salt comprising reacting
   $HO-CH_2-CH_2-NH-NH_2$ and m HX to obtain [$HO-CH_2-CH_2-NH_2-NH_2^+][X^-$] or [$HO-CH_2-CH_2-NH_2-NH_3^{2+}][X^-]_2$
   where HX=$HNO_3$, $HClO_4$, $HN(NO_2)_2$ or $HC(NO_2)_3$ and m=1 or 2.

2. The method of claim 1 conducted in a polar solvent selected from the group of methanol, ethanol, isopropanol, n-propanol, n-butanol, water and acetonitrile.

3. A method for preparing 1:1 salts comprising reacting; $HO-CH_2-CH_2-NH-NH_2$ and HX to obtain [$HO-CH_2-CH_2-NH_2-NH_2^+][X^-$]
   where HX=$HNO_3$, $HClO_4$, $HN(NO_2)_2$ and $HC(NO_2)_3$.

4. The method of claim 3 carried out in a suitable, dry inert atmosphere from −25° C. to +25° C., and in a polar solvent selected from the group of methanol, ethanol, isopropanol, n-propanol, n-butanol, water, and acetonitrile.

5. A method for preparing 1:2 salts comprising; reacting $HO-CH_2-CH_2-NH-NH_2$ and 2 HX to obtain [$HO-CH_2-CH_2-NH_2-NH_3^{2+}][X^-]_2$ where HX=$HNO_3$ or $HClO_4$.

6. The method of claim 5 carried out in a suitable, dry inert atmosphere from −25° C. to +25° C., and in a polar solvent selected from the group of methanol, ethanol, isopropanol, n-propanol, n-butanol, water, and acetonitrile.

7. The method of claim 1 wherein the acid is added in a concentration of 30–100 wt %.

8. The method of claim 1 for preparing a nitrate salt of HEH comprising; reacting $HO-CH_2-CH_2-NH-NH_2$ and $HNO_3$ to obtain [$HO-CH_2-CH_2-NH_2-NH_2$]$^+$ [$ClO_4$].

9. The method of claim 1 for preparing a perchlorate salt of HEH comprising; reacting HO—CH$_2$—CH$_2$—NH—NH$_2$ and HClO$_4$ to obtain [HO—CH$_2$—CH$_2$—NH—NH$_2$]$^+$ [ClO$_4$]$^-$.

10. The method of claim 1 for preparing a dinitramide salt of HEH comprising; reacting HO—CH$_2$—CH$_2$—NH—NH$_2$ and HN(NO$_2$)$_2$ to obtain [HO—CH$_2$—CH$_2$—NH—NH$_3$$^+$] [N[NO$_2$)$_2$$^-$].

11. The method of claim 1 for preparing nitroformate salt of HEH comprising, reacting HO—CH—CH$_2$—NH—NH$_2$ and HC(NO$_2$)$_3$ to obtain [HO—CH$_2$—CH$_2$—NH—NH$_2$]$^+$ [C(NO$_2$)$_3$]$^-$.

12. The method of claim 1 for preparing a dinitrate salt of HEH comprising; ting HO—CH$_2$—CH$_2$—NH—NH$_2$ and 2 HNO$_3$ to obtain [HO—CH$_2$—CH$_2$—NH—NH$_3$]$^{2+}$$_2$.

13. The method of claim 1 for preparing a diperchlorate salt of HEH comprising; reacting HO—CH$_2$—CH$_2$—NH—NH$_2$ and 2 HClO$_4$ to obtain [HO—CH$_2$—CH$_2$—NH—NH$_3$]$^{2+}$[ClO$_4$$^-$]$_2$.

14. A salt of hydroxyethylhydrazine (HEH) selected from the group of [HO—CH$_2$—CH$_2$—NH—NH$_2$$^+$][X$^-$] and [HO—CH$_2$—CH$_2$—NH$_2$—NH$_3$$^{2+}$][X$^-$]$_2$ where X=NO$_3$, ClO$_4$, N(NO$_2$)$_2$ or C(NO$_2$)$_3$.

15. At least one salt of claim 14 employed in mixtures or eutectics with compounds selected from the group of ammonium nitrate, ammonium perchlorate, ammonium dinitramide, hydroxylammonium nitrate, hydroxylammonium perchlorate, hydroxylammonium dinitramide, lithium nitrate, lithium dinitramide, lithium perchlorate, nitric acid (30–100% wt %), inhibited fuming red nitric acid (IRFNA) and perchloric acid (30–70% wt %).

16. At least one salt of claim 14 employed in a monopropellant or an explosive.

17. A salt of hydroxyethylhydrazine (HEH) selected from the group of [HO—CH$_2$—CH$_2$—NH$_2$—NH$_2$$^+$][X$^-$] and of [HO—CH$_2$—CH$_2$—NH$_2$—NH$_3$$^{2+}$][X$^-$]$_2$ where X=ClO$_4$.

18. The salt of claim 17 having the formula: [HO—CH$_2$—CH$_2$—NH$_2$—NH$_2$$^+$][ClO$_4$$^-$].

19. The salt of claim 17 having the formula: [HO—CH$_2$—CH$_2$—NH$_2$—NH$_3$$^{2+}$][ClO$_4$$^-$]$_2$.

* * * * *